US009629631B2

(12) United States Patent
Nicholas et al.

(10) Patent No.: US 9,629,631 B2
(45) Date of Patent: Apr. 25, 2017

(54) COMPOSITE DRIVE BEAM FOR SURGICAL STAPLING

(71) Applicant: Covidien LP, Mansfield, MA (US)

(72) Inventors: David A. Nicholas, Trumball, CT (US); John W. Beardsley, Wallingford, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 394 days.

(21) Appl. No.: 14/507,886

(22) Filed: Oct. 7, 2014

(65) Prior Publication Data

US 2016/0000436 A1  Jan. 7, 2016

Related U.S. Application Data

(60) Provisional application No. 62/019,560, filed on Jul. 1, 2014.

(51) Int. Cl.
*A61B 17/072* (2006.01)
*A61B 17/10* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC ............... A61B 17/068; A61B 17/072; A61B 17/07207; A61B 17/115; A61B 17/1155;
(Continued)

(56) References Cited

U.S. PATENT DOCUMENTS

| 4,637,539 A * | 1/1987 | Turcott | ............... B25B 27/30 |
| | | | 173/128 |
| 6,269,997 B1 * | 8/2001 | Balazs | ............. A61B 17/115 |
| | | | 227/175.1 |

(Continued)

FOREIGN PATENT DOCUMENTS

| CN | 101288594 A | 10/2008 |
| EP | 0705570 A1 | 4/1996 |

(Continued)

OTHER PUBLICATIONS

Extended European Search Report issued in corresponding EP15174466 dated Nov. 13, 2015.

*Primary Examiner* — Scott A. Smith (57) ABSTRACT

An end effector includes a mounting portion that mounts to a surgical stapling apparatus, first and second jaw members extending distally from the mounting portion, a drive beam engagable with the first and second jaw members, and a threaded drive screw. The first jaw member includes a first tissue engaging surface and the second jaw member supports a fastener cartridge. The fastener cartridge includes a second tissue engaging surface that defines fastener retaining slots that support fasteners. The drive beam includes a retention foot formed of a first material. The retention foot defines a threaded bore that supports a threaded insert formed of a second material. The threaded drive screw is threadably engaged with the threaded insert and is rotatable to distally advance the drive beam along the threaded drive screw to fire and form the fasteners.

20 Claims, 10 Drawing Sheets

(51) Int. Cl.
*A61B 17/068* (2006.01)
*A61B 17/3211* (2006.01)
*A61B 17/115* (2006.01)
*A61B 17/00* (2006.01)

(52) U.S. Cl.
CPC ......... *A61B 17/3211* (2013.01); *A61B 17/115* (2013.01); *A61B 2017/0046* (2013.01); *A61B 2017/00314* (2013.01); *A61B 2017/00367* (2013.01); *A61B 2017/00398* (2013.01); *A61B 2017/00734* (2013.01); *A61B 2017/00964* (2013.01); *A61B 2017/07214* (2013.01); *A61B 2017/07278* (2013.01)

(58) Field of Classification Search
CPC A61B 2017/07214; A61B 2017/00398; A61B 2017/07278
USPC .. 227/19, 175.1, 176.1, 178.1, 180.1, 175.2; 606/139, 153, 219
See application file for complete search history.

(56) References Cited

U.S. PATENT DOCUMENTS

| | | | |
|---|---|---|---|
| 8,366,087 B2 * | 2/2013 | McAdoo | B25H 1/10 227/154 |
| 8,469,254 B2 | 6/2013 | Czernik et al. | |
| 8,899,462 B2 * | 12/2014 | Kostrzewski | A61B 17/07207 227/175.1 |
| 2007/0158385 A1 * | 7/2007 | Hueil | A61B 17/07207 227/175.1 |
| 2008/0078801 A1 * | 4/2008 | Shelton | A61B 17/072 227/175.1 |
| 2009/0101692 A1 | 4/2009 | Whitman et al. | |
| 2011/0121049 A1 | 5/2011 | Malinouskas et al. | |
| 2011/0290853 A1 * | 12/2011 | Shelton, IV | A61B 17/07207 227/177.1 |
| 2011/0290855 A1 * | 12/2011 | Moore | A61B 17/072 227/180.1 |
| 2012/0199632 A1 * | 8/2012 | Spivey | A61B 17/07207 227/176.1 |
| 2012/0273550 A1 | 11/2012 | Scirica | |
| 2012/0298719 A1 * | 11/2012 | Shelton, IV | A61B 17/07207 227/176.1 |
| 2013/0098966 A1 | 4/2013 | Kostrzewski et al. | |
| 2013/0098968 A1 * | 4/2013 | Aranyi | A61B 17/07207 227/177.1 |
| 2013/0098970 A1 * | 4/2013 | Racenet | A61B 17/07207 227/180.1 |

FOREIGN PATENT DOCUMENTS

| | | |
|---|---|---|
| EP | 2586381 A1 | 5/2013 |
| EP | 2898838 A1 | 7/2015 |
| WO | 2008045383 A2 | 4/2008 |

* cited by examiner

COMPOSITE DRIVE BEAM FOR SURGICAL STAPLING

CROSS-REFERENCE TO RELATED APPLICATIONS

This application claims the benefit of and priority to U.S. Provisional Patent Application No. 62/019,560, filed Jul. 1, 2014, the entire disclosure of which is incorporated by reference herein.

TECHNICAL FIELD

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting, and/or stapling tissue.

BACKGROUND

A number of surgical device manufacturers have developed product lines with proprietary drive systems for operating and/or manipulating electromechanical surgical devices. Some electromechanical surgical devices include a handle assembly, which is reusable, and replaceable loading units and/or single use loading units or the like that are selectively connected to the handle assembly prior to use and then disconnected from the handle assembly following use, in order to be disposed of or in some instances sterilized for re-use. These loading units can include jaw members that support an actuatable drive beam to effectuate clamping, cutting, and/or stapling of tissue.

Many of these electromechanical surgical devices, or components thereof, are relatively expensive to manufacture, purchase, and/or operate. There is a desire by manufacturers and end users to develop electromechanical surgical devices that are relatively inexpensive to manufacture, purchase, and/or operate.

Accordingly, a need exists for electromechanical surgical apparatus, devices and/or systems that are relatively economical to develop and manufacture, to store and ship, as well as economical and convenient to purchase and use from the end user's perspective.

SUMMARY

According to one aspect of the present disclosure, an end effector of a surgical stapling apparatus is provided. The end effector includes a mounting portion adapted to selectively mount to the surgical stapling apparatus, first and second jaw members extending distally from the mounting portion, a drive beam engagable with the first and second jaw members, and a threaded drive screw.

The first jaw member includes a first tissue engaging surface and defines a ramp. The second jaw member is adapted to support a fastener cartridge. The fastener cartridge includes a second tissue engaging surface that defines fastener retaining slots. The fastener retaining slots support a plurality of fasteners.

The drive beam is engagable with the ramp of the first jaw member to maintain the first jaw member and the second jaw member in an approximated state as the drive beam distally translates along the first and second jaw members.

The drive beam includes a retention foot formed of a first material. In embodiments, the first material includes metallic material. In some embodiments, the first material includes stainless steel. The retention foot defines a threaded bore that supports a threaded insert formed of a second material. In embodiments, the second material includes polymeric material. In some embodiments, the second material includes polyether ether ketone. The threaded bore includes internal threads that extend from an inner surface of the threaded bore. The internal threads engage external threads extending from an outer surface of the threaded insert. The threaded insert includes opposite ends. In embodiments, each of the opposite ends of the threaded insert includes locking flanges extending therefrom to fix the threaded insert to the retention foot.

In some embodiments, the threaded insert includes internal threads extending from an internal surface of the threaded insert. In embodiments, each of the internal threads of the threaded insert defines an internal peak and each of the external threads of the threaded insert defines an external peak, each internal peak being adjacent to, and longitudinally offset from, one of the external peaks.

In embodiments, the drive beam supports a knife adapted to cut tissue as the drive beam translates along the threaded drive screw. In some embodiments, the drive beam includes a lateral projecting member, wherein at least portions of the lateral projecting member are formed of a polymeric material.

The threaded drive screw is threadably engaged with the threaded insert of the drive beam. The threaded drive screw is rotatable to selectively distally advance the drive beam along the threaded drive screw to fire the plurality of fasteners from the fastener retaining slots of the fastener cartridge and form the plurality of fasteners against the first tissue engaging surface of the first jaw member.

In another aspect of the present disclosure, a powered surgical stapling apparatus includes a handle assembly, a shaft assembly extending distally from the handle assembly, and an end effector selectively detachable from the shaft assembly.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION OF EMBODIMENTS

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Figure 1:
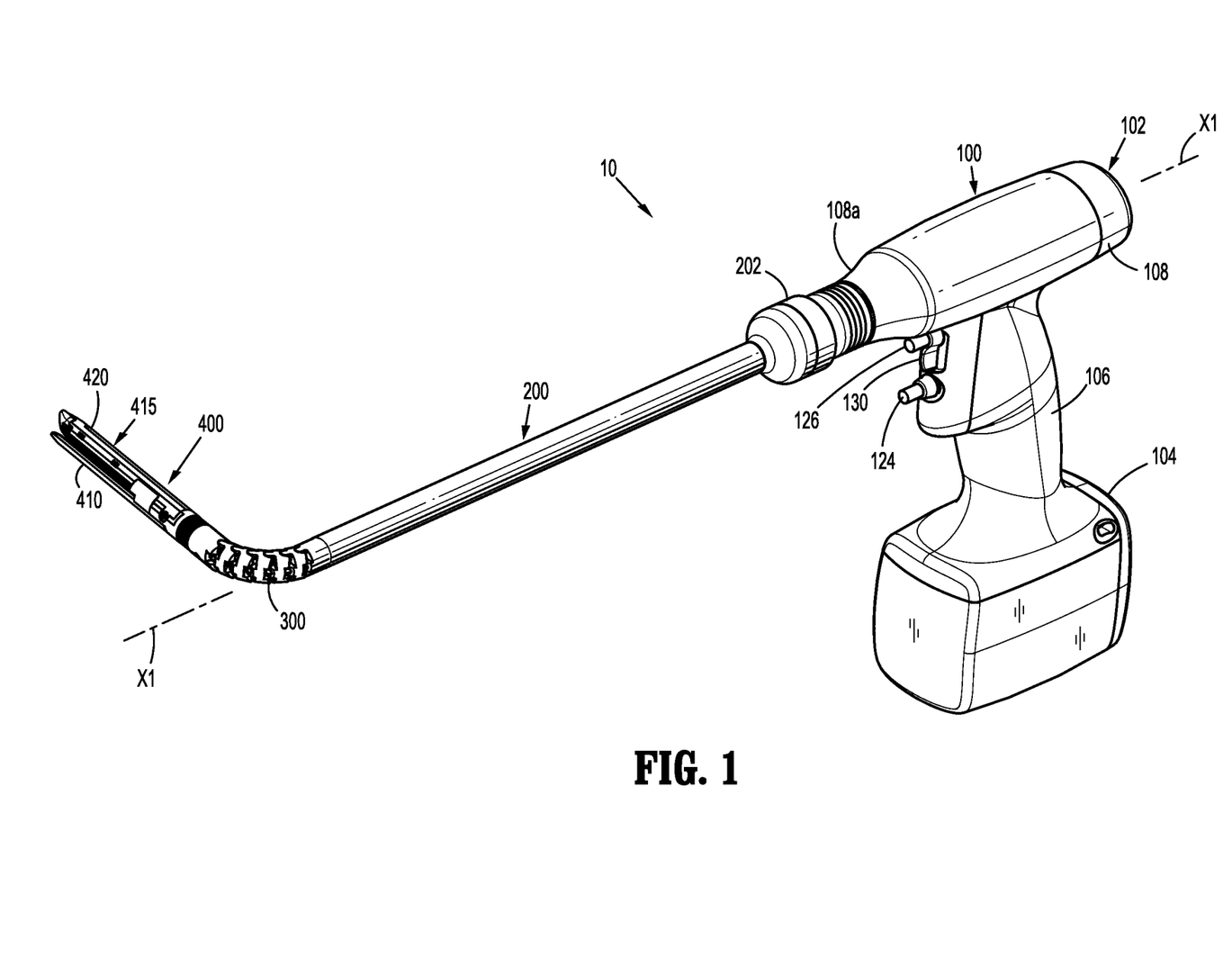
FIG. 1 is a perspective view of an electromechanical surgical system according to the principles of the present disclosure.
Figure 2:
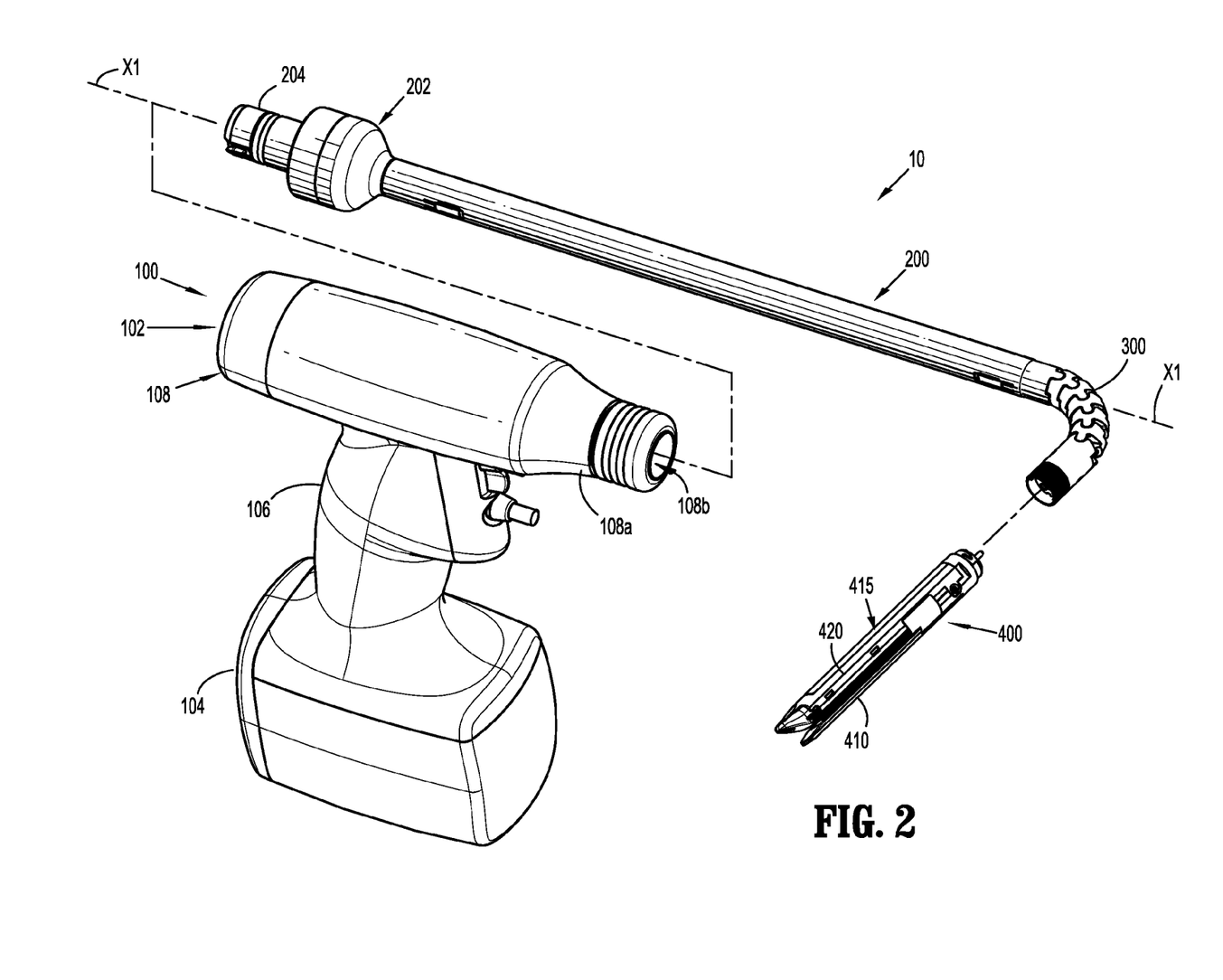
FIG. 2 is a perspective view, with parts separated, of the electromechanical surgical system of FIG. 1.

Referring initially to FIGS. 1 and 2, an electromechanical, hand-held, powered surgical system is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200 that are each configured for actuation and manipulation by the electromechanical, hand-held, powered surgical instrument 100. In particular, surgical instrument 100 is configured for selective connection with an articulation assembly 300 of shaft assembly 200, and, in turn, shaft assembly 200 is configured for selective connection with any one of a plurality of different end effectors 400 via articulation assembly 300.

Reference may be made to U.S. Patent Application Publication No. 2009/0101692, U.S. Patent Application Publication No. 2011/0121049, and U.S. Patent Application Publication No. 2013/0098966, the entire content of each of which is hereby incorporated herein by reference, for a detailed description of the construction and operation of exemplary electromechanical, hand-held, powered surgical instruments, the components of which are combinable and/or interchangeable with one or more components of powered surgical system 10 described herein.

Generally, as illustrated in FIGS. 1 and 2, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106. The surgical instrument 100 has a controller (not shown) for controlling certain functions of the surgical system, collecting data, and performing other functions. Instrument housing 102 defines a cavity (not shown) therein in which a circuit board (not shown) and a drive mechanism (not shown) are situated.

The circuit board is configured to control the various operations of surgical instrument 100, as will be set forth in additional detail below. In accordance with the present disclosure, instrument housing 102 provides a housing in which a rechargeable battery (not shown), is removably situated. The battery is configured to supply power to any of the electrical components of surgical instrument 100.

Upper housing portion 108 of instrument housing 102 has a nose or connecting portion 108a configured to accept a corresponding shaft coupling assembly 204 of transmission housing 202 of shaft assembly 200. As seen in FIG. 2, connecting portion 108a of upper housing portion 108 of surgical instrument 100 defines a cylindrical recess 108b that receives shaft coupling assembly 204 of transmission housing 202 of shaft assembly 200 when shaft assembly 200 is mated to surgical instrument 100. The connecting portion 108a of the surgical instrument 100 has at least one rotatable drive member. In some embodiments, connecting portion 108a houses a plurality of rotatable drive members or connectors (not shown), each drive member of the plurality of drive members can be independently, and/or dependently, actuatable and rotatable by the drive mechanism (not shown) housed within instrument housing 102.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X1" (see FIGS. 1 and 2), relative to instrument housing 102; to move a first/upper jaw member or anvil assembly 410 of end effector 400 relative to a second/lower jaw member or cartridge assembly 420 of end effector 400; to articulate and/or rotate the shaft assembly 200; and/or to fire a fastener cartridge 420a within cartridge assembly 420 of end effector 400.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive members or connectors of surgical instrument 100, at a given time.

As illustrated in FIGS. 1 and 2, instrument housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in instrument housing 102 includes, for each one of the control buttons 124, 126 and rocker device(s) 130, respective Hall-effect switches (not shown) that are actuated by the movement of the magnets in the control buttons 124, 126 and rocker device(s) 130. The actuation of Hall-effect switch (not shown), corresponding to control buttons 124, 126 causes the circuit board to provide appropriate signals to the function selection module and the input drive component of the drive mechanism to open/close end effector 400 and/or to fire a stapling/cutting cartridge within end effector 400.

Similarly, the actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to instrument housing 102 of surgical instrument 100. Specifically, movement of rocker device 130 in a first direction causes end effector 400 and/or shaft assembly 200 to rotate relative to instrument housing 102 in a first direction, while movement of rocker device 130 in an opposite, e.g., second, direction causes end effector 400 and/or shaft assembly 200 to rotate relative to instrument housing 102 in an opposite, e.g., second, direction.

Turning now to FIGS. 3-13, end effector 400 is shown and described. End effector 400 is configured and adapted to apply a plurality of linear rows of fasteners "F" (e.g., staples, see FIG. 5). In certain embodiments, the fasteners are of various sizes, and, in certain embodiments, the fasteners have various lengths or rows, e.g., about 30, 45 and 60 mm in length.

Figures 3, 4:
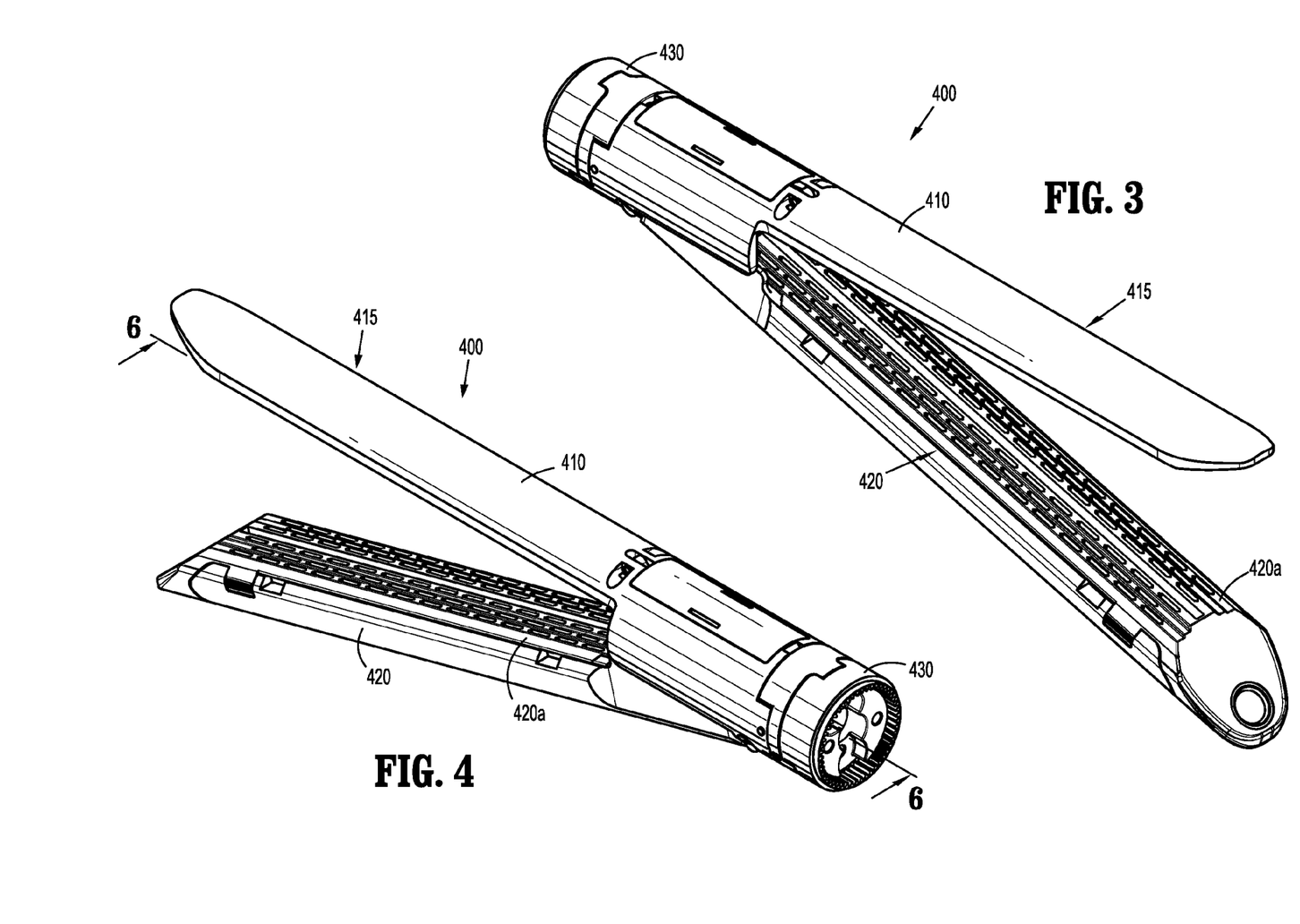
FIG. 3 is a front, perspective view of an end effector of the electromechanical surgical system of FIGS. 1 and 2.
FIG. 4 is a rear, perspective view of the end effector of FIG. 3.

As seen in FIGS. 3 and 4, end effector 400 includes a mounting portion 430 coupled to a jaw assembly 415. A proximal end portion of mounting portion 430 is configured for selective connection to a distal end portion of shaft assembly 200 (e.g., articulation assembly 300) that has complementary structure formed thereon. Jaw assembly 415 is connected to, and extends distally from, mounting portion 430. Jaw assembly 415, as will be discussed in greater detail below, includes lower jaw member 420, which is configured to selectively support fastener cartridge 420a therein, and upper jaw member 410, each of which is secured to mounting portion 430 to enable relative movement between upper and lower jaw members 410, 420. Jaw assembly 415 is pivotally movable to orient upper and lower jaw members 410, 420 between approximated and unapproximated states.

Figure 5:
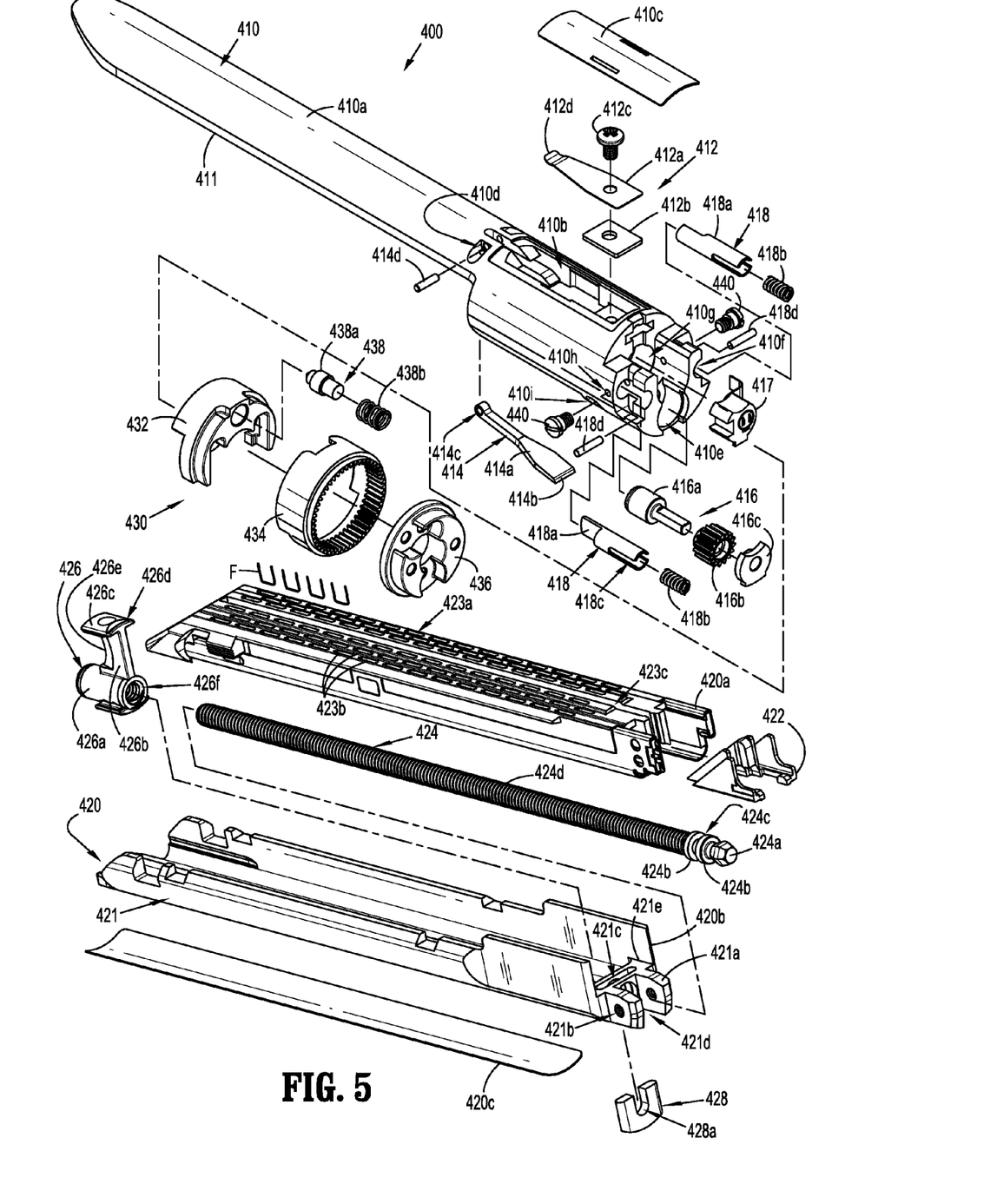
FIG. 5 is a perspective view, with parts separated, of the end effector of FIGS. 3 and 4.

With reference to FIG. 5, upper jaw member 410 includes an anvil body 410a with a tissue engaging/fastener forming surface 411 including a plurality of staple forming pockets (not shown), arranged in longitudinally extending rows and configured to form the fasteners upon a firing of end effector 400, as appreciated by one skilled in the art. Anvil body 410a supports a leaf spring assembly 412 and a lever assembly 414 that are supported within a chamber 410b of body 410a. Leaf spring assembly 412 and lever assembly 414 are enclosed within chamber 410b by a cover 410c that is selectively removable from body 410a. Together, leaf spring assembly 412 and lever assembly 414 function to bias jaw assembly 415 in the unapproximated state and enable pivotal movement of the jaw assembly 415 between the approximated and unapproximated states as described in greater detail herein.

Leaf spring assembly 412 includes a leaf spring 412a that is mounted to body 410a at a first end of leaf spring 412a by a mounting plate 412b and a fastener 412c. Leaf spring 412a extends to an engagement tip 412d at a second end of leaf spring 412a that can have any suitable configuration such as a curvilinear scoop.

Lever assembly 414 includes a lever 414a that defines a pin channel 414c on one end thereof and a distal tip 414b on an opposite end thereof. Lever 414 is pivotally mounted to anvil body 410a by a pin 414d that is received through pin channel 414c of lever 414a and a pin channel 410d defined in anvil body 410a.

Anvil body 410a defines a plurality of bores on a proximal end of anvil body 410a including a drive bore 410e that receives a drive assembly 416, a pair of plunger bores 410f that receives a pair of plunger assemblies 418, and a electrical contact bore 410g that receives an electrical contact member 417 that functions to electrically communicate with instrument housing 102 when end effector 400 is secured to shaft assembly 200. Drive assembly 416 includes a drive member 416a, a gear member 416b coupled to drive member 416a, and a mounting plate 416c that supports drive member 416a and gear member 416b. Each plunger assembly of the pair of plunger assemblies 418 includes a plunger 418a that receives a spring 418b that functions to spring bias plunger 418a in a distal direction to facilitate securement of fastener cartridge 420a to cartridge assembly 420. Plunger 418a defines a pin slot 418c that receives a pin 418d to secure each plunger assembly within a respective one of the pair of plunger bores 410f when pin 418d is received within a pin channel 410h defined within anvil body 410a.

Lower jaw member 420 is configured and adapted to selectively receive fastener cartridge 420a. Fastener cartridge 420a includes a tissue engaging surface 423a that defines a plurality of rows of fastener retaining slots 423b adapted to support the plurality of fasteners "F" (and a plurality of staple pushers, not shown, but can be appreciated by those skilled in art). Fastener cartridge 420a also includes a longitudinally extending knife slot 423c disposed between pairs of rows of fastener retaining slots 423b that is adapted to enable drive beam 426 to axially translate therethrough.

Lower jaw member 420 includes a mounting member 420b, in the form of a channel that supports fastener cartridge 420a and a base member 420c couplable to mounting member 420b. Mounting member 420b includes a mounting body 421 having a pair of wings 421a that extends proximally therefrom. The pair of wings 421a defines a fastener channel 421b therethrough that is dimensioned to receive fasteners 440 advanced into a pair of passages 410i defined in upper jaw member 410 for securing upper jaw member 410 to lower jaw member 420. A slot 421c and a screw passage 421d are defined in a plate 421e of mounting body 421 positioned adjacent to the pair of wings 421a.

An actuation sled 422 is supported by lower jaw member 420 and is adapted to advance through fastener cartridge 420a to fire the plurality of fasteners supported with fastener cartridge 420a as one skilled in the art will appreciate. Lower jaw member 420 rotatably supports a drive screw 424 therein that extends substantially an entire length of lower jaw member 420. Drive screw 424 is threadably engaged with drive beam 426, which is axially slidably supported in lower jaw member 420 between proximal and distal positions in response to rotation of drive screw 424, as described in greater detail below. Drive screw 424 includes a multi-faceted head 424a, a pair of retention members 424b that define an annular channel 424c therebetween, and a distally extending threaded shaft 424d. Drive screw 424 extends through screw passage 421d so that a bracket 428, which defines a U-shaped channel 428a therethrough, secures drive screw 424 to mounting member 420b when bracket 428 is received in slot 421c and positioned within annular channel 424c. Bracket 428 and mounting member 420b cooperate to axially and lateral fix drive screw 424 in lower jaw member 420 while enabling drive screw 424 to rotate.

Drive beam 426 has a substantially I-shaped cross-sectional profile configured to progressively approximate lower jaw member 420 and upper jaw member 410 as drive beam 426 travels through knife slot 423c in fastener cartridge 420a. Drive beam 426 functions to axially displace actuation sled 422 through lower jaw member 420 and includes a retention foot 426a having an internally threaded bore 426f, a vertically oriented support strut 426b supported on retention foot 426a, and a lateral projecting member 426c formed atop support strut 426b. Lateral projecting member 426c defines a notch 426d formed in an upper surface thereof. Vertically oriented support strut 426b supports a knife 426e thereon that is adapted to cut tissue.

FIG. 5 illustrates that mounting portion 430 is secured to the proximal end portion of upper jaw member 410. Mounting portion 430 includes a first member 432, a second member 434, and a third member 436 that are coupled together and support a spring assembly 438. Spring assembly 438 includes a plunger 438a and a spring 438b.

Figure 6:
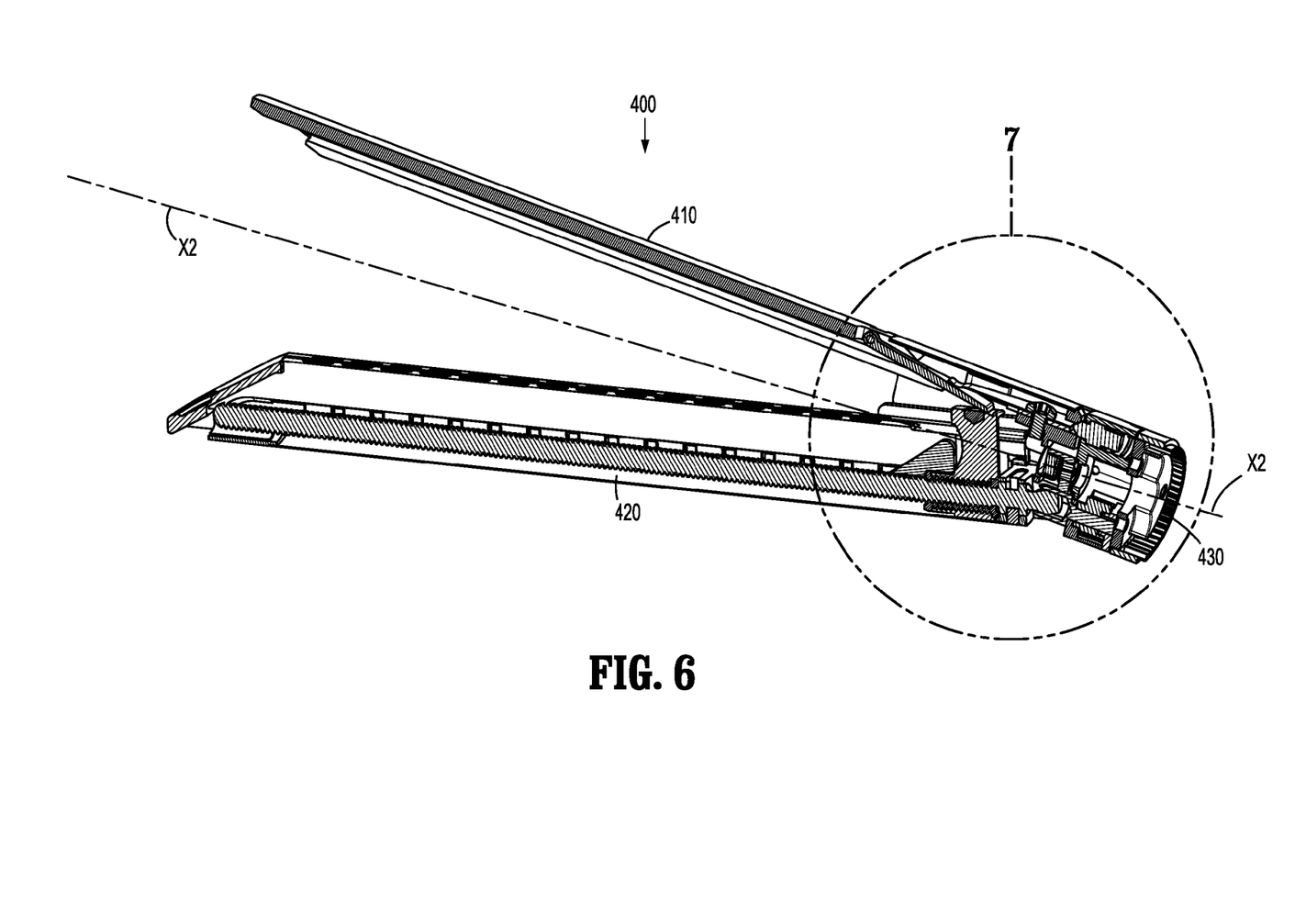
FIG. 6 is a side, cross-sectional, perspective view of the end effector of FIGS. 3-5, as taken through 6-6 of FIG. 4, showing the end effector in an unapproximated state.
Figure 7:
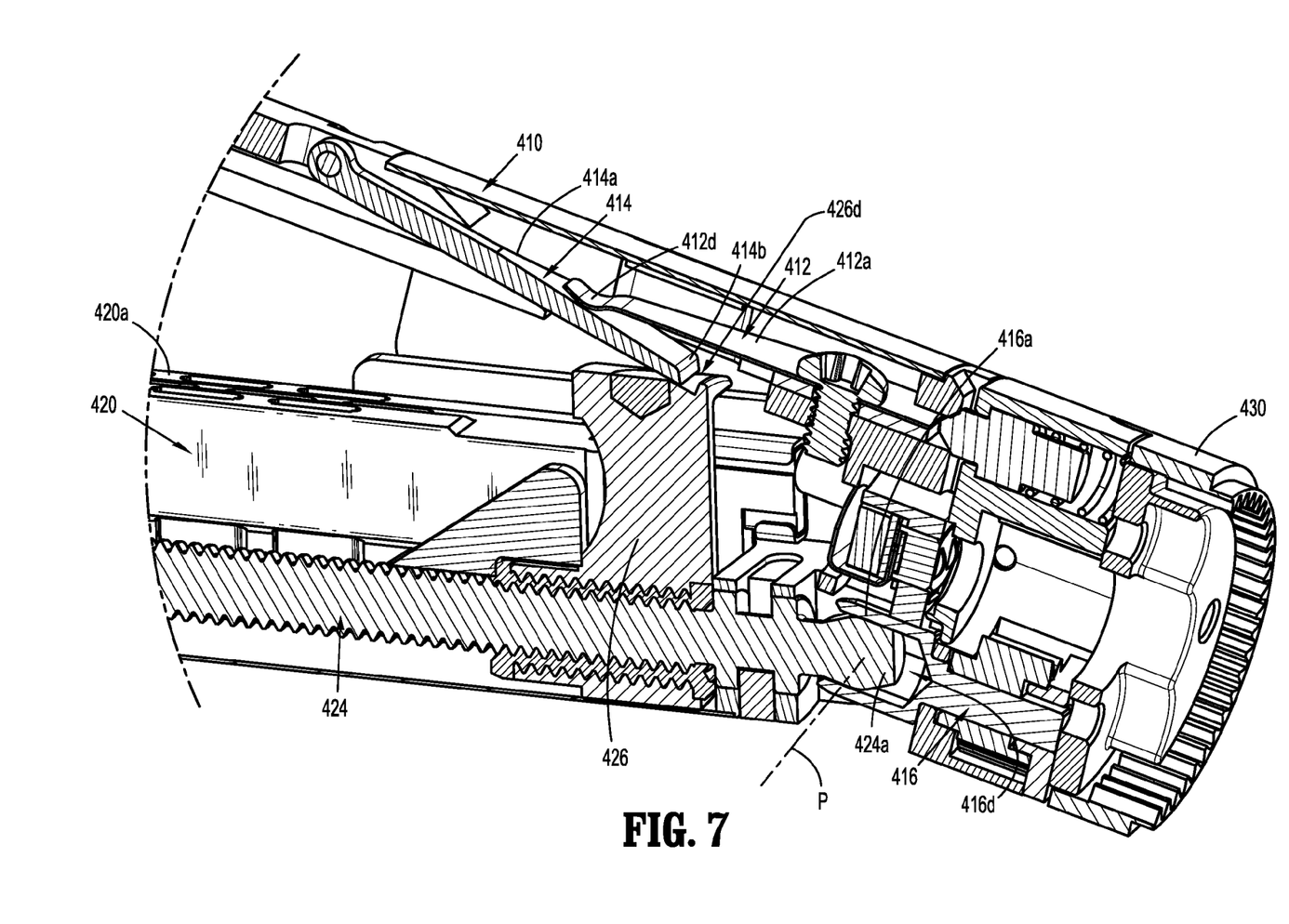
FIG. 7 is an enlarged view of the indicated area of detail shown in FIG. 6.

Referring now to FIGS. 6 and 7, end effector 400 is shown in an initial and/or unapproximated state, in which upper jaw member 410 is spaced from lower jaw member 420 relative to a longitudinal axis "X2" defined through end effector 400. In the unapproximated state, lower jaw member 420 is positioned at an acute angle (e.g., 15 degrees) relative to upper jaw member 410, drive screw 424 is disposed at an acute angle relative to mounting portion 430, and head 424a of drive screw 424 is supported at an acute angle within a bore 416d defined by drive member 416a.

As depicted in FIG. 7, when end effector 400 is in the unapproximated state, lever 414a is disposed in an extended position, due to spring biasing forces applied to lever 414a by leaf spring assembly 412, through contact with engagement tip 412d of leaf spring 412a. Drive beam 426 is disposed in a proximal-most position and leaf spring 412a of leaf spring assembly 412 is disposed in an unflexed state. In the extended position of lever 414a, distal tip 414b of lever 414a is disposed in notch 426d of lateral projecting member 426c of drive beam 426.

Figure 8:
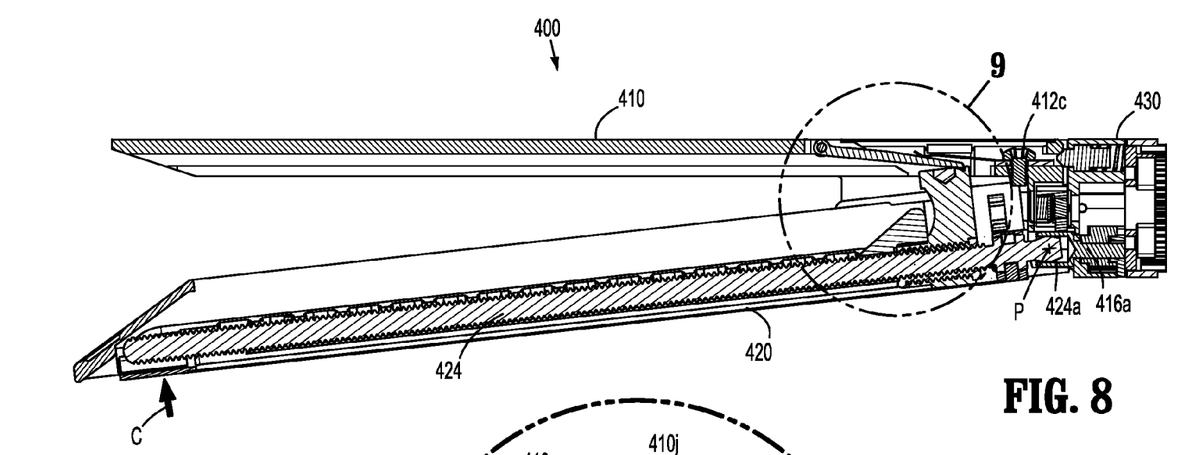
FIG. 8 is a side, cross-sectional view of the end effector showing a drive beam thereof in a partially advanced position.
Figure 9:
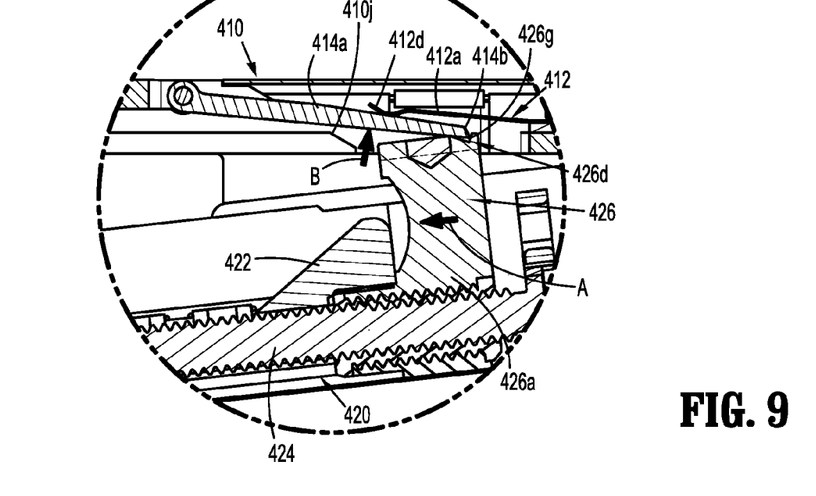
FIG. 9 is an enlarged view of the indicated area of detail shown in FIG. 8.

With reference to FIGS. 8 and 9, rotation of drive member 416a rotates head 424a of drive screw 424, which imparts rotation to drive screw 424. The pair of retention members 424b maintains drive screw 424 longitudinally fixed as the drive member 416a imparts rotational movement to drive screw 424. With drive screw 424 being threadably engaged with retention foot 426a of drive beam 426, rotational movement of drive screw 424 distally translates drive beam 426, as indicated by arrow "A." In this regard, distal tip 414b of lever 414a engages a notch sidewall 426g of drive beam 426, preventing distal translation of drive beam 426 and causing lower jaw member 420 to pivot relative to upper jaw member 410 in the direction indicated by arrow "B" and about a pivot axis "P" that is defined transversely through head 424a of drive screw 424. As lower jaw member 420 pivots toward upper jaw member 410, closing and/or approximating upper and lower jaw members 410, 420, drive beam 426 engages a bottom surface of lever 414a so that lever 414a pivots, counterclockwise (as illustrated in FIG. 9, albeit clockwise when viewed from the opposite side of end effector 400), toward upper jaw member 410 in the direction indicated by arrow "B" against spring biasing forces applied to a top surface of lever 414a through engagement tip 412d of leaf spring assembly 412. In response to pivoting movement of lever 414a toward upper jaw member 410, leaf spring 412a begins to flex to a flexed state in the direction indicated by arrow "B" so that leaf spring 412a pivots, clockwise (as illustrated in FIG. 9, albeit counterclockwise when viewed from the opposite side of end effector 400), relative to fastener 412c, toward upper jaw member 410.

Figures 10, 11:
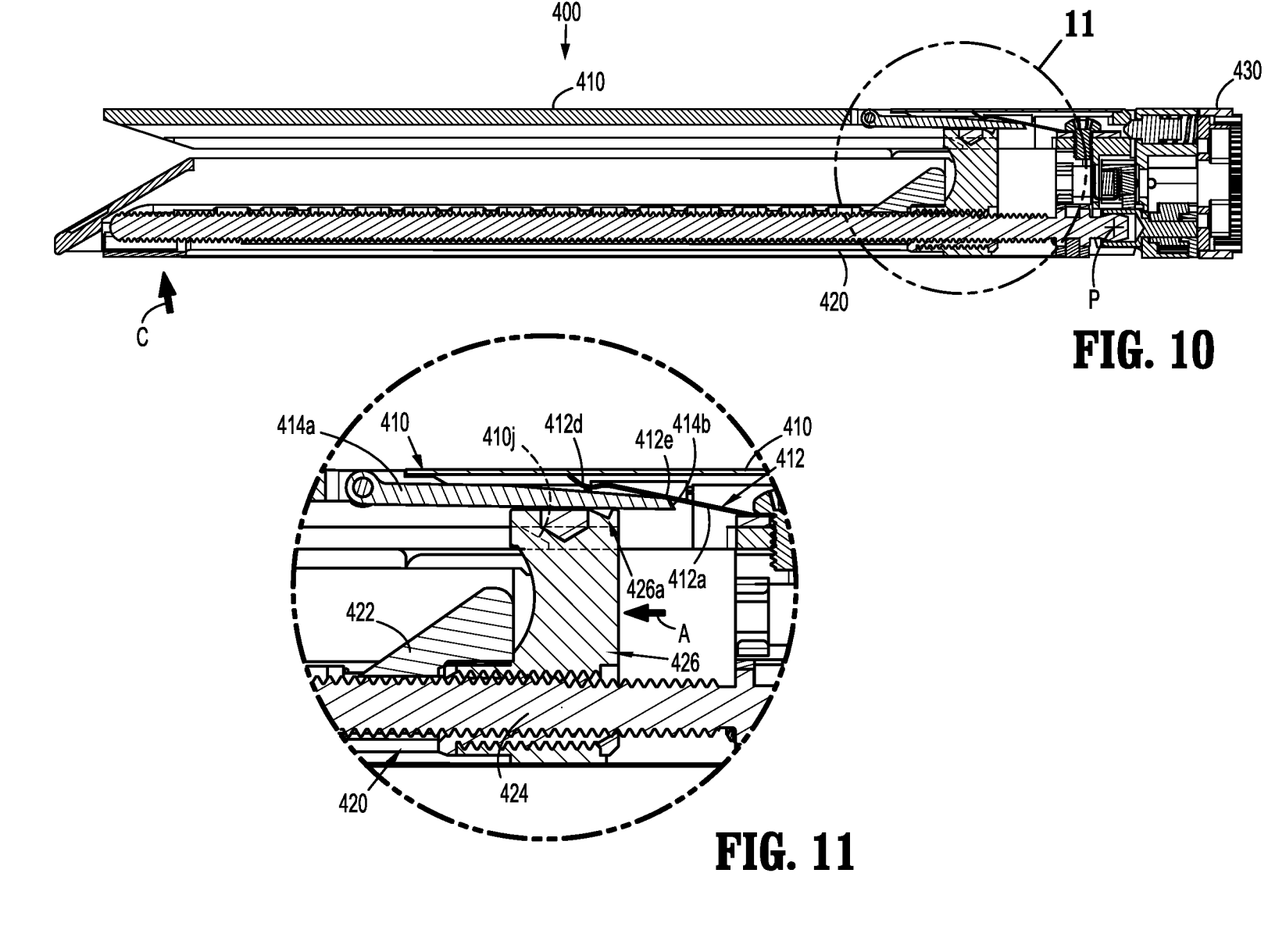
FIG. 10 is a side, cross-sectional view of the end effector in an approximated state with the drive beam thereof shown in a partially advanced position.
FIG. 11 is an enlarged view of the indicated area of detail shown in FIG. 10.

As seen in FIGS. 10 and 11, further rotational movement of drive screw 424 pivots lever 414a so that distal tip 414b of lever 414a separates from notch 426a enabling lever 414a to pivot toward a retracted position and enabling lower jaw member 420 to continue to pivot toward upper jaw member 410, as indicated by arrow "C," until upper and lower jaw members 410, 420 are positioned in the approximated state. Upon separation of distal tip 414b of lever 414a and notch 426a of drive beam 426, continued rotational movement of drive screw 424 distally translates drive beam 426, as indicated by the arrow "A," beneath lever 414a along the bottom surface of lever 414a or lever assembly 414 until drive beam 426 mounts to ramp 410j. Distal translation of drive beam 426 drives lever 414a to the retracted position in which distal tip 414b engages a bottom surface of leaf spring 412a at a point 412e along leaf spring 412a, separating engagement tip 412d from a top surface of lever 414a and enabling drive beam 426 to mount to, and translate along, ramp 410j.

Figure 12:
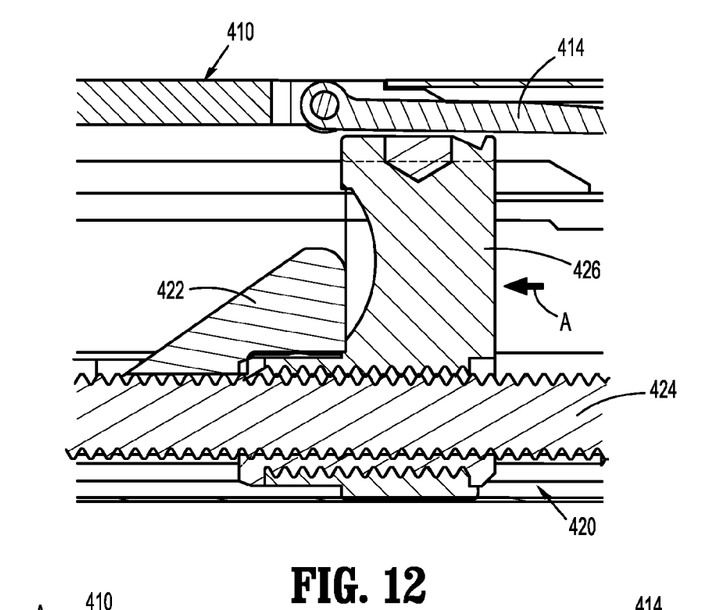
FIG. 12 is an enlarged, partial, cross-sectional view of the end effector showing the drive beam partially advanced.
Figure 13:
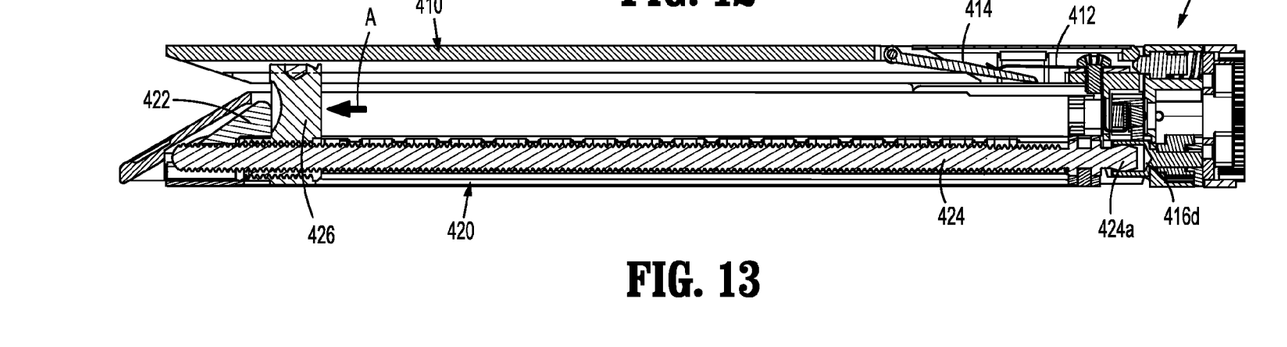
FIG. 13 a side, cross-sectional view of the end effector in an approximated state with the drive beam thereof shown in a distally advanced position.

With reference to FIGS. 12 and 13, when upper and lower jaw members 410, 420 are in the approximated state, lower jaw member 420 is positioned in parallel with upper jaw member 410, and head 424a of drive screw 424 is supported within a bore 416d of drive member 416a so that drive screw 424 is parallel to upper jaw member 410. In the approximated state, continued rotation of drive screw 424 distally translates drive beam 426 through end effector 400 toward a distal end portion of end effector 400, as indicated by arrow "A." Upon translating drive beam 426, distally past lever assembly 414, leaf spring assembly 412 urges lever assembly 414 to the extended position. Continued rotation of drive screw 424 advances actuation sled 422 through fastener cartridge 420a to fire the plurality of fasteners stored within fastener cartridge 420a for securing to tissue.

Drive screw 424 can then be rotated in an opposite direction to retract drive beam 426 proximally to the proximal-most position. More particularly, drive beam 426 is retracted proximally until drive beam 426 engages lever assembly 414, which under the spring bias of leaf spring assembly 412, urges upper and lower jaw members 410, 420 apart so that upper and lower jaw members 410, 420 are disposed in the original or unapproximated state as shown in FIG. 6. Fastener cartridge 420a can then be removed, disposed of, and/or replaced, as desired, and the operation of end effector 400 described above can be repeated as necessary with a new, un-fired fastener cartridge 420a loaded in lower jaw member 420.

In embodiments, end effector 400 supports one or more computer or microchips (not shown) that electrically communicate signals or identification codes to the controller and/or circuit board of surgical instrument 100. The signals or identification codes can indicate whether or not fastener cartridge 420a, or portions thereof, is at least partially fired, unfired, etc.

Figure 14:
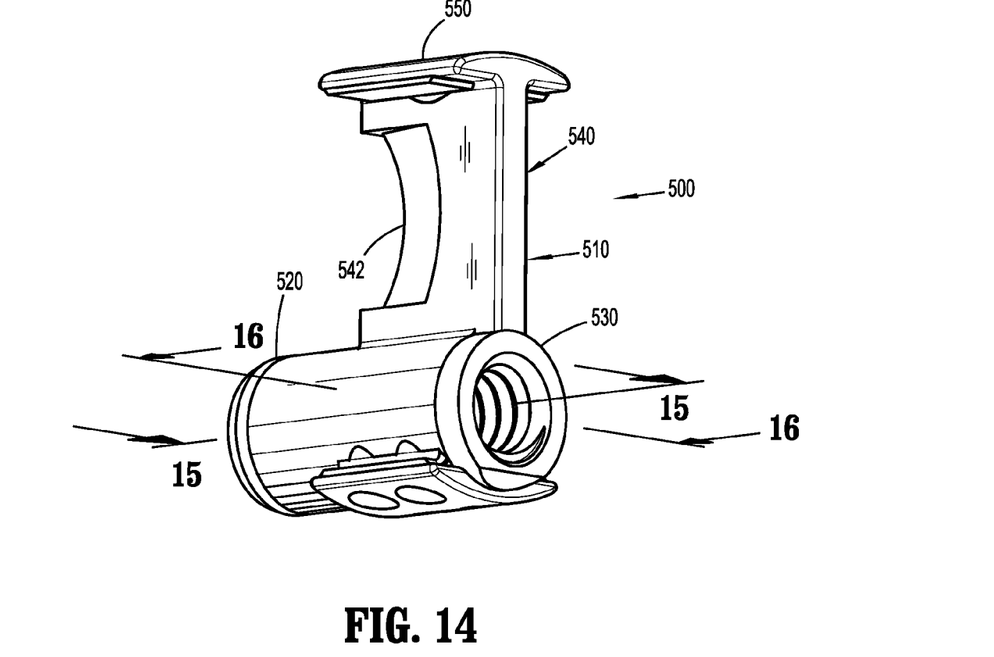
FIG. 14 is a rear, perspective view of an embodiment of a drive beam in accordance with the principles of the present disclosure.
Figure 15:
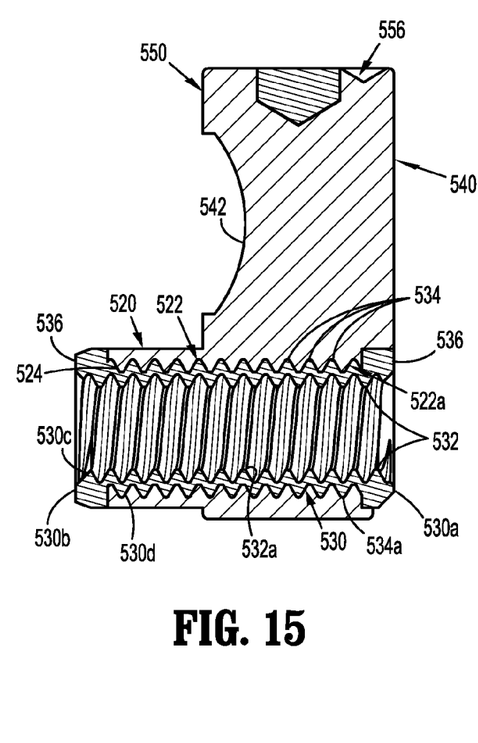
FIG. 15 is a side, cross-sectional view of the drive beam of FIG. 14, as taken through line 15-15 of FIG. 14.
Figure 16:
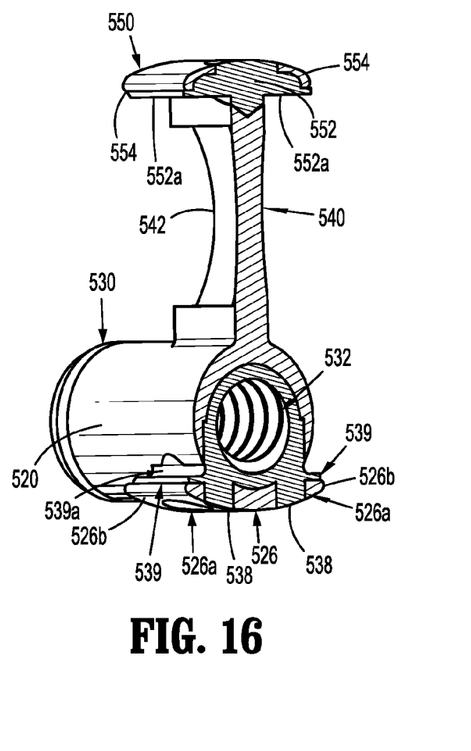
FIG. 16 is a rear, perspective, cross-sectional view of the drive beam of FIG. 14, as taken through line 16-16 of FIG. 14.

Turning now to FIGS. 14-16, a drive beam, in accordance with another embodiment of the present disclosure, is generally designated as 500. Drive beam 500 is substantially similar to drive beam 426, and thus, will only be described in detail herein to the extent necessary to describe differences in construction and/or operation from those of drive beam 426.

Drive beam 500 includes a composite body 510 that is formed of two or more materials to reduce input torque for advancing drive beam 500 while providing strength sufficient to support loads required to clamp and fire fasteners in thick tissue. Composite body 510 has an I-shaped cross-sectional profile (see FIG. 16) and includes a retention foot 520, a threaded insert 530 secured to the retention foot 520, a vertically oriented support strut 540 extending from retention foot 520, and a lateral projecting member 550 formed atop support strut 530. Vertically oriented support strut 540 supports a knife 542 adapted to cut tissue as drive beam 500 translates along threaded drive screw 424.

In some embodiments, at least portions of one or more of retention foot 520, vertically oriented support strut 540, and/or lateral projecting member 550 can be integrally and/or monolithically formed of a first material, for example, a metallic material such as stainless steel to provide load supporting strength for clamping and firing fasteners "F" with the presently described surgical devices. In embodiments, at least portions of one or both of threaded insert 530 and/or lateral projecting member 550 can be integrally and/or monothically formed of a second material, for example, a polymeric material such as polyether ether ketone (PEEK) to reduce input torque for advancing drive beam 500 as described in greater detail below. As can be appreciated, one or more of any of the components, or portions thereof, of drive beam 500 can be formed of any suitable material including polymeric and/or metallic materials. Persons skilled in the art will understand that one or more of any of the components, or portions thereof, can be formed using known forming and/or fastening techniques such as molding, casting, milling, welding, etc. For example, metallic materials of drive beam 500 can be casted and/or milled and polymeric materials can be injection molded therein.

As seen in FIG. 15, retention foot 520 defines a threaded bore 522 having an inner surface 522a. Threaded bore 522 includes internal threads 524 that extend from inner surface 522a of threaded bore 522. Retention foot 520 further includes a heel 526 extending from a bottom portion of an outer surface of retention foot 520. Heel 526 defines one or more channels 526a therein and includes a plurality of wings 526b extending laterally therefrom.

Threaded insert 530 extends between opposite ends 530a, 530b and includes internal threads 532 and external threads 534 that depend therefrom. Internal threads 532 are formed on/extend from an internal/inner surface 530c of threaded insert 530 and external threads 534 are formed on/extend from an external/outer surface 530d of threaded insert 530. Internal threads 524 of threaded bore 522 engage external threads 534 extending from outer surface 530d of threaded insert 530. Each of internal threads 532 of threaded insert 530 defines an internal peak 532a and each of external threads 534 of threaded insert 530 defines an external peak 534a. In embodiments, each internal peak 532a is adjacent to, and longitudinally offset from, one of external peaks 534a. As can be appreciated, one or more of any of the threads of retention foot 520 and/or threaded insert 530 can have any suitable configuration including any suitable shape and/or dimension.

Each of opposite ends 530a, 530b of threaded insert 530 includes a locking flange 536 extending radially outward therefrom to fix and/or facilitate securement of threaded insert 530 to retention foot 520. Threaded insert 530 can include one or more locking tabs 538 extending from a bottom surface of threaded insert 530. Each locking tab 538 is secured within one of channels 526a of heel 526 to fix and/or facilitate securement of threaded insert 530 to retention foot 520. Threaded insert 530 can include a pair of wings 539 extending from locking tabs 538 that overly the pair of wings 526b of heel 526.

As seen in FIGS. 15 and 16, lateral projecting member 550 includes a central portion 552 and a pair of wings 554 extending from central portion 552. Portions of central portion 552 and/or the pair of wings 554 can define a notch 556 formed in an upper surface of lateral projecting member 550. Central portion 552 can be formed of a polymeric material such as PEEK and the pair of wings 554 can be formed of a metallic material such as stainless steel. A bottom surface 552a of central portion 552 is adapted to engage and slide along ramp 410j of first jaw member 410.

In operation, threaded drive screw 424 is threadably engaged with threaded insert 530 of drive beam 500. Threaded drive screw 424 is rotatable to selectively distally advance drive beam 500 along threaded drive screw 424. As threaded drive screw 424 rotates, drive beam 500 advances similar to that described above with respect to drive beam 426. Lateral projecting member 500, namely bottom surface 552a of central portion 552 engages with, and slides along, the top surface of ramp 410j (see FIG. 11) of first jaw member 410 to maintain first jaw member 410 and second jaw member 420 in an approximated state as drive beam 500 distally translates along first and second jaw members 410, 420. As drive beam 500 distally translates, the plurality of fasteners "F" are fired from fastener retaining slots 423b of fastener cartridge 420a to form the plurality of fasteners "F" against tissue engaging surface 411 of first jaw member 410.

As noted above, threaded insert 530, or portions thereof, can be formed of any suitable polymeric material such as PEEK to reduce friction forces generated between outer surfaces of threaded drive screw 424 and inner surfaces of threaded insert 530 of drive beam 500 upon rotation of threaded drive screw 424. Similarly, central portion 552 of lateral projecting member 550A and can also be formed of polymeric material to reduce friction forces between bottom surface 552a of lateral projecting member 550 and the first jaw member 410 (e.g., the top surfaces of ramp 410j), which can be metallic. Likewise, the pair of wings 539 of threaded insert 530 can be formed of polymeric material to reduce friction forces between upper surfaces 539a of the pair of wings 539 and surfaces (e.g., metallic) of second jaw member 420. Reduction in friction forces between threaded drive screw 424 and drive beam 500; upper surfaces 539a of the pair of wings 539 and second jaw member 420; and/or between bottom surface 552a of lateral projecting member 550 and first jaw member 410 reduces input torque required to advance drive beam 500 along threaded drive screw 424. For example, friction forces generated by plastic-on-metal engagement can be up to two and a half times less than a similar metal-on-metal engagement. Given that portions of drive beam 500 can be formed of metallic material, composite body 510 of drive beam 500 provides sufficient strength to support loads required to clamp and fire fasteners in thick tissue while simultaneously reducing input torque required to advance drive beam 500 along threaded drive screw 424.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. An end effector of a surgical stapling apparatus, the end effector comprising:
a mounting portion adapted to selectively mount to the surgical stapling apparatus;
a first jaw member extending distally from the mounting portion, the first jaw member including a first tissue engaging surface;
a second jaw member extending distally from the mounting portion and adapted to support a fastener cartridge, the fastener cartridge including a second tissue engaging surface that defines fastener retaining slots, the fastener retaining slots supporting a plurality of fasteners;
a drive beam engagable with the first and second jaw members, the drive beam including a retention foot formed of a first material, the retention foot defining a threaded bore, the threaded bore supporting a threaded insert formed of a second material; and
a threaded drive screw being threadably engaged with the threaded insert of the drive beam and rotatable to selectively distally advance the drive beam along the threaded drive screw to fire the plurality of fasteners from the fastener retaining slots of the fastener cartridge and form the plurality of fasteners against the first tissue engaging surface of the first jaw member.

2. The end effector of claim 1, wherein the first material includes metallic material and the second material includes polymeric material.

3. The end effector of claim 2, wherein the first material includes stainless steel.

4. The end effector of claim 2, wherein the second material includes polyether ether ketone.

5. The end effector of claim 1, wherein the first jaw member defines a ramp, the drive beam being engagable with the ramp to maintain the first jaw member and the second jaw member in an approximated state as the drive beam distally translates along the first and second jaw members.

6. The end effector of claim 1, wherein the drive beam supports a knife adapted to cut tissue as the drive beam translates along the threaded drive screw.

7. The end effector of claim 1, wherein the threaded bore includes internal threads that extend from an inner surface of the threaded bore and engage external threads extending from an outer surface of the threaded insert, and wherein the threaded insert includes opposite ends, each of the opposite ends of the threaded insert including locking flanges extending therefrom to fix the threaded insert to the retention foot.

8. The end effector of claim 7, wherein the threaded insert includes internal threads extending from an internal surface of the threaded insert.

9. The end effector of claim 8, wherein each of the internal threads of the threaded insert defines an internal peak and each of the external threads of the threaded insert defines an external peak, each internal peak being adjacent to, and longitudinally offset from, one of the external peaks.

10. The end effector of claim 1, wherein the drive beam includes a lateral projecting member, wherein at least portions of the lateral projecting member are formed of a polymeric material.

11. A powered surgical stapling apparatus, comprising:
a handle assembly;
a shaft assembly extending distally from the handle assembly; and
an end effector selectively detachable from the shaft assembly, the end effector including:
a first jaw member having a first tissue engaging surface;
a second jaw member adapted to support a fastener cartridge, the fastener cartridge including a second tissue engaging surface that defines fastener retaining slots, the fastener retaining slots supporting a plurality of fasteners;
a drive beam engagable with the first and second jaw members, the drive beam including a retention foot formed of a first material, the retention foot defining a threaded bore, the threaded bore supporting a threaded insert formed of a second material; and
a threaded drive screw being threadably engaged with the threaded insert of the drive beam and rotatable to selectively distally advance the drive beam along the threaded drive screw to fire the plurality of fasteners from the fastener retaining slots of the fastener cartridge and form the plurality of fasteners against the first tissue engaging surface of the first jaw member.

12. The powered surgical stapling apparatus of claim 11, wherein the first material includes metallic material and the second material includes polymeric material.

13. The powered surgical stapling apparatus of claim 12, wherein the first material includes stainless steel.

14. The powered surgical stapling apparatus of claim 12, wherein the second material includes polyether ether ketone.

15. The powered surgical stapling apparatus of claim 11, wherein the first jaw member defines a ramp, the drive beam being engagable with the ramp to maintain the first jaw member and the second jaw member in an approximated state as the drive beam distally translates along the first and second jaw members.

16. The powered surgical stapling apparatus of claim 11, wherein the drive beam supports a knife adapted to cut tissue as the drive beam translates along the threaded drive screw.

17. The powered surgical stapling apparatus of claim 11, wherein the threaded bore includes internal threads that extend from an inner surface of the threaded bore and engage external threads extending from an outer surface of the threaded insert, and wherein the threaded insert includes opposite ends, each of the opposite ends of the threaded insert including locking flanges extending therefrom to fix the threaded insert to the retention foot.

18. The powered surgical stapling apparatus of claim 17, wherein the threaded insert includes internal threads extending from an internal surface of the threaded insert.

19. The powered surgical stapling apparatus of claim 18, wherein each of the internal threads of the threaded insert defines an internal peak and each of the external threads of the threaded insert defines an external peak, each internal peak being adjacent to, and longitudinally offset from, one of the external peaks.

20. The powered surgical stapling apparatus of claim 11, wherein the drive beam includes a lateral projecting member, wherein at least portions of the lateral projecting member are formed of a polymeric material.

* * * * *